United States Patent
Brown et al.

(10) Patent No.: US 10,031,066 B1
(45) Date of Patent: Jul. 24, 2018

(54) LINEAR POLARIZATION RESISTANCE FLEX SENSORS AND METHODS THAT INVOLVE STRUCTURE AS WORKING ELECTRODE(S)

(71) Applicant: Analatom Incorporated, Sunnyvale, CA (US)

(72) Inventors: Douglas W. Brown, Sunnyvale, CA (US); Richard J. Connolly, Sunnyvale, CA (US); Duane R. Darr, Foster City, CA (US); Vinod S. Agarwala, Sunnyvale, CA (US)

(73) Assignee: ANALATOM INCORPORATED, Santa Clara, CA (US)

( * ) Notice: Subject to any disclaimer, the term of this patent is extended or adjusted under 35 U.S.C. 154(b) by 315 days.

(21) Appl. No.: 14/752,815

(22) Filed: Jun. 26, 2015

Related U.S. Application Data

(60) Provisional application No. 62/017,799, filed on Jun. 26, 2014.

(51) Int. Cl.
*G01N 27/07* (2006.01)
*G01N 17/02* (2006.01)
*G01N 17/04* (2006.01)

(52) U.S. Cl.
CPC ............ *G01N 17/02* (2013.01); *G01N 17/04* (2013.01)

(58) Field of Classification Search
CPC ............................ G01N 17/02; G01N 27/026
See application file for complete search history.

(56) References Cited

U.S. PATENT DOCUMENTS

| | | | |
|---|---|---|---|
| 4,222,006 A * | 9/1980 | Schneider | G01N 27/404 204/408 |
| 5,259,944 A * | 11/1993 | Feliu | G01N 17/02 204/404 |
| 5,310,470 A | 5/1994 | Agarwala et al. | |
| 2002/0190729 A1 | 12/2002 | Wilson | |
| 2006/0006137 A1 | 1/2006 | NiBlock | |

OTHER PUBLICATIONS

Thomas & Betts product description for the Blackburn® G5 Direct-Burial Rebar Grounding Clamp, published 2009, downloaded Aug. 28, 2017.*
Texas Instrument Application Report SN0A514C—Apr. 2008—Revised May 2013 AN-1798 Designing with Electro-Chemical Sensors.*

(Continued)

*Primary Examiner* — Alexander S Noguerola
(74) *Attorney, Agent, or Firm* — DLA Piper LLP (US)

(57) ABSTRACT

Systems and methods are disclosed for monitoring corrosion of a structure by using the structure itself as part of the electrochemical measurement. According to some implementations, linear polarization resistance (LPR) sensor devices for direct monitoring of corrosion on a structure are presented. According to certain innovations herein, a sensor device may include three electrodes, such as a counter electrode, a reference electrode, and a working electrode comprised of the structure being monitored. In further embodiments, each electrode may be configured on a polymer flexible substrate cable such as polyimide, with each electrode fabricated from a noble metal, for example, gold-plated copper, or metal systems in which the exterior surface will not oxidize from environmental exposure.

16 Claims, 14 Drawing Sheets

(56) References Cited

OTHER PUBLICATIONS

PCT International Search Report of PCT/US15/38184; dated Dec. 1, 2015; (4 pgs.).
PCT Written Opinion of the International Searching Authority of PCT/US15/38184; dated Dec. 1, 2015; (10 pgs.).
PCT International Preliminary Report on Patentability of PCT/US15/38184; dated Dec. 27, 2016; (1 pg.).

* cited by examiner

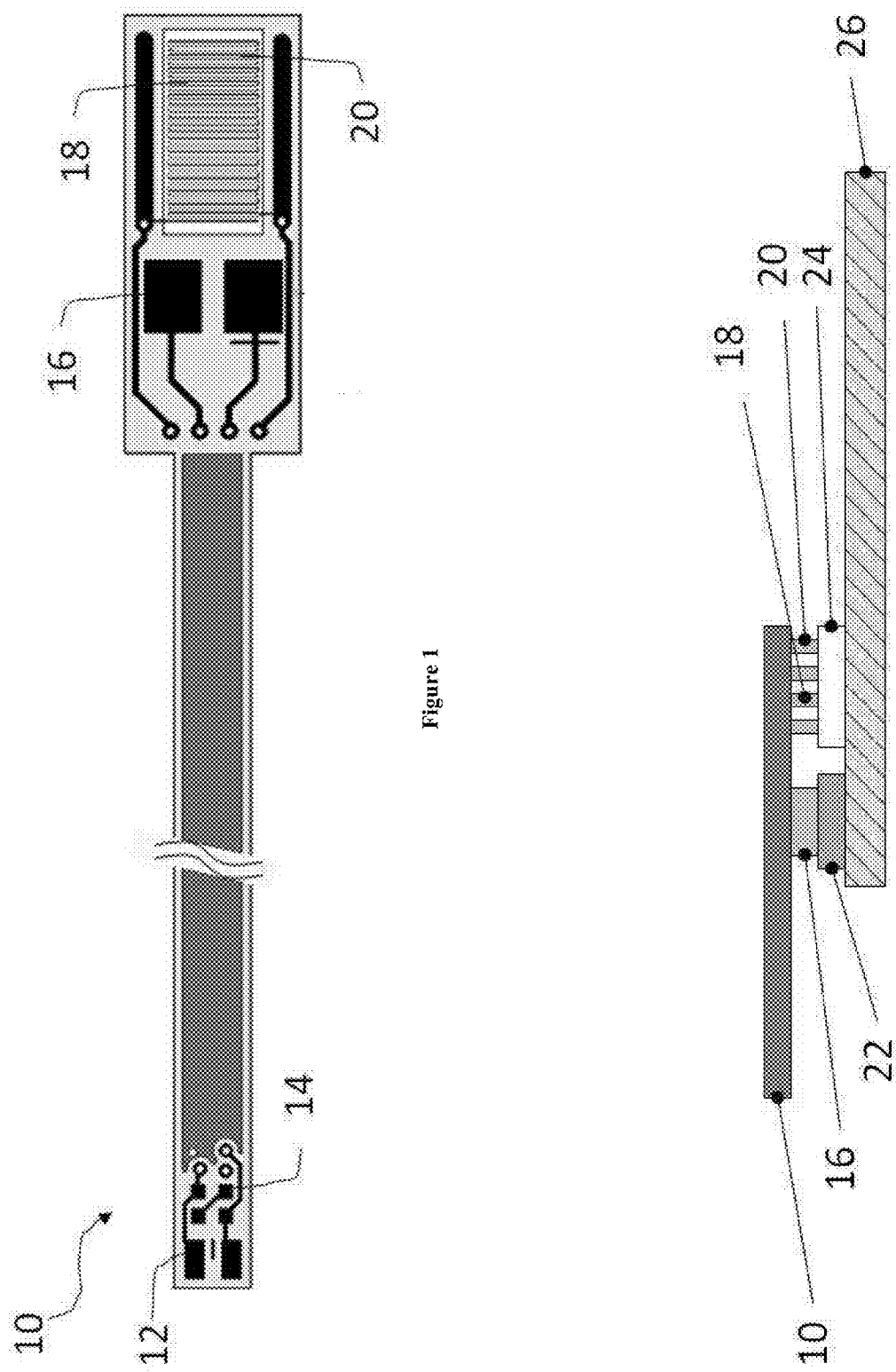

LINEAR POLARIZATION RESISTANCE FLEX SENSORS AND METHODS THAT INVOLVE STRUCTURE AS WORKING ELECTRODE(S)

CROSS-REFERENCE TO RELATED APPLICATION(S)

This application claims benefit/priority of U.S. provisional patent application No. 62/017,799, filed Jun. 26, 2014, which is incorporated herein by reference in entirety.

BACKGROUND

Field

Aspects of the present innovations relate generally to systems and methods of monitoring corrosion of a structure by using the structure itself as part of the electrochemical measurement.

Description of Related Information

Corrosion sensors can be distinguished by the following categories, direct or indirect and intrusive or non-intrusive. Direct corrosion monitoring measures a response signal, such as current or potential, generated as a direct result of oxidation-reduction reactions. Examples of common direct corrosion monitoring techniques are: corrosion coupons, electrical resistance (ER), electro-impedance spectroscopy (EIS), and linear polarization resistance (LPR) techniques. Whereas, indirect corrosion monitoring techniques measure an outcome of the corrosion process, two of the most common indirect techniques are ultrasonic testing and radiography. An intrusive measurement requires access to the structure. Corrosion coupons, ER, EIS, and LPR probes are intrusive since they have to access the structure. Non-intrusive techniques include ultrasonic testing and radiography.

Each of these methods has advantages and disadvantages. Corrosion coupons provide the most reliable physical evidence possible. Unfortunately, coupons usually require significant time in terms of labor and provide time averaged data that cannot be utilized for real time or on-line corrosion monitoring. ER probes provide a basic measurement of metal loss, but unlike coupons, the value of metal loss can be measured at any time, as frequently as required, while the probe is in situ and permanently exposed to the structure. The disadvantage is ER probes require calibration with material properties of the structure to be monitored. The advantage of the LPR technique is that the measurement of corrosion rate is made instantaneously. This is a more powerful tool than either coupons or ER where the fundamental measurement is metal loss and where some period of exposure is required to determine corrosion rate. The disadvantage to the LPR technique is that it can only be successfully performed in relatively clean aqueous electrolytic environments. EIS is a very powerful technique that provides both kinetic (corrosion rate) and mechanistic information. The main disadvantages associated with the use of EIS are that the instrumentation is sophisticated and sometimes difficult to use in the field due to the length of time required for each frequency sweep. Additionally, interpretation of the data can be difficult. Finally, ultrasonic testing and radiography can be used to detect and measure (depth) corrosion through non-destructive and non-intrusive means. The disadvantage with the ultrasonic testing and radiography equipment is the same with corrosion coupons, both require significant time in terms of labor and cannot be utilized for real-time or on-line corrosion monitoring.

There are also various micro-fabricated sensor device for monitoring deterioration of a structure. Such devices may include a first electrode having a first finger and a second electrode having a second finger. The second finger is positioned about apart from the first finger by about 1 mm or less. The current flow between the first electrode and the second electrode correlates with a degree of deterioration of the electrodes.

DESCRIPTION OF THE DRAWINGS

The accompanying drawings, which constitute a part of this specification, illustrate various implementations and aspects of the innovations herein and, together with the description, help illustrate the principles of the present inventions. In the drawings:

FIG. 1 is a schematic diagram of a micro linear polarization resistance flex sensor consistent with one or more aspects of the innovations herein.

FIG. 2 is a schematic diagram of the micro linear polarization resistance flex sensor attached to the structure consistent with one or more aspects of the innovations herein.

DETAILED DESCRIPTION OF ILLUSTRATIVE IMPLEMENTATIONS

Figure 3:
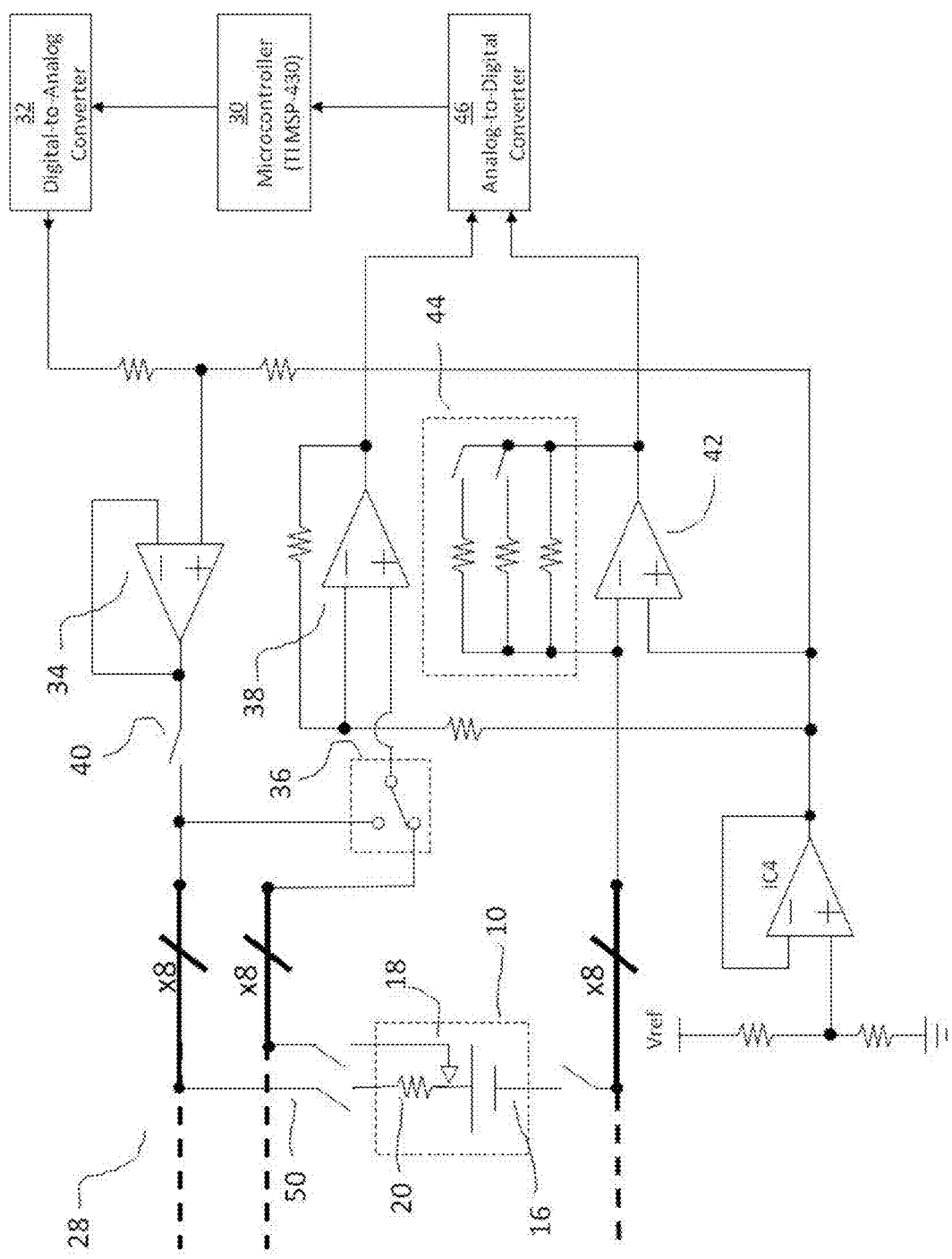
FIG. 3 is a schematic diagram of instrumentation amplifier circuitry that may be used in the sensor device consistent with one or more aspects of the innovations herein.

Reference will now be made in detail to the inventions herein, examples of which are illustrated in the accompanying drawings. The implementations set forth in the following description do not represent all implementations consistent with the present inventions. Instead, they are merely some examples consistent with certain aspects related to the present innovations. Wherever possible, the same reference numbers will be used throughout the drawings to refer to the same or like parts.

Systems and methods of linear polarization resistance (LPR) sensor devices for direct monitoring of corrosion on a structure are presented. According to certain innovations herein, for example, a sensor device may include three electrodes. In further embodiments, each electrode may be configured on a polymer flexible substrate cable such as polyimide, with each electrode fabricated from a noble metal, for example, gold-plated copper, or metal systems in which the exterior surface will not oxidize from environmental exposure. According to various exemplary implementations, the first two electrodes may be fabricated with a thickness of about 1 to about 10 mils and a length of about 0.1 mm to about 20 mm. Further, such electrode pair may be configured in an interdigitated fashion with a separation distance of about 10 mils or less. The flexible substrate cable (flex cable) may contain a porous scrim or membrane material between the pair of electrodes and the structure being monitored. Such scrim may further provide electrical insulation between the interdigitated electrodes and the structure. A third electrode may be placed about 10 mm or less from the first two and makes electrical contact to the structure by placing an electrically conductive transfer tape (e.g., 1 mil thick, etc) between the electrode and structure. The flex cable can be attached to the structure through the use of adhesives or in the case of placement in a butt joint or lap joint configuration, the holding force is provided by the joint itself. Corrosion may be computed from known physical constants and by measuring the polarization resistance measured between the electrolytic solution and the structure using the three electrodes. Additionally, the time of wetness and salinity is computed from look-up tables and measuring the resistance between the interdigitated electrode pair.

Additionally, implementations herein describe systems and methods for monitoring corrosion in a structure. Such a system may include a plurality of LPR sensors, an electronic controller, a multiplexing network, and electronic components attached to a polyimide flex circuit carrier. Each of the LPR sensors includes a working electrode and a reference electrode. The electronic controller is programmed to read measurements from each of the LPR sensors. The multiplexing network enables the controller to address each of the LPR sensors, and electronic components match the LPR sensors to the controller. The polyimide flex circuit carrier includes passivated metal interconnects and bond pads onto which the LPR sensors, the electronic components, the electronic controller, and the multiplexing network are attached.

According to other implementations, systems and methods of preparing a sensor device are provided. For example, such a method may include providing an electrically conductive material having a first surface and a second surface in substantially parallel planes with respect to each other. Further, in some implementations, the first surface may be photolithographically patterned with a first electrode having first fingers and a second electrode having second fingers, and the patterned electrodes are etched partway between the first surface and the second surface. The partly-etched electrically conductive material is mounted on a carrier with the first surface contacting the carrier and heated to be bonded. The second surface may be photolithographically patterned with the first and the second electrodes that are aligned with the etched portions of the first surface, and the patterns are etched until the first and the second electrodes are formed.

Linear Polarization Resistance

Corrosion of metals takes place when the metal dissolves due to oxidation and reduction reactions occurring at the interface of metal and electrolyte solutions. This process occurs by electrochemical half-reactions; (1) an anodic (oxidation) reaction involving dissolution of metals in the electrolyte and release of electrons, and (2) a cathodic (reduction) reaction involving gain of electrons by the electrolyte species like atmospheric oxygen, $O_2$, $H_2O$, or $H^+$ ions in an acid. The flow of electrons from the anodic reaction sites to the cathodic reaction sites creates a corrosion current. Under normal circumstances, this electrochemically generated current is below the limits of detection, however when an external potential is briefly applied, these values can be accurately measured to obtain a polarization curve. Application of an external potential exponentially increases the anodic and cathodic currents, which allows instantaneous corrosion rates to be ascertained from the polarization curve. Extrapolation of these polarization curves back to their linear region provides the corrosion current, which is then used to calculate the rate of corrosion.

Electrochemical technique of linear polarization resistance (LPR) is used to study corrosion processes since the corrosion reactions are electrochemical reactions occurring on the metal surface. Modern corrosion studies are based on the concept of mixed potential theory postulated by Wagner and Traud, which states the net corrosion reaction is the sum of independently occurring oxidation and reduction. For the case of metallic corrosion in presence of an aqueous medium, the corrosion process can be written as, $$M + zH_2O \underset{b}{\overset{f}{\leftrightarrow}} M^{z+} + \frac{z}{2}H_2 + zOH^-, \quad (1)$$

where z is the number of electrons lost per atom of the metal. This reaction is the result of an anodic (oxidation) reaction $$M \underset{b}{\overset{f}{\leftrightarrow}} M^{z+} + ze^-, \quad (2)$$

and a cathodic (reduction) reaction, $$zH_2O + ze^- \underset{b}{\overset{f}{\leftrightarrow}} \frac{z}{2}H_2 + zOH^-. \quad (3)$$

It is assumed that the anodic and cathodic reactions occur at a number of sites on a metal surface and that these sites change in a dynamic statistical distribution with respect to location and time. Thus, during corrosion of a metal surface, metal ions are formed at anodic sites with the loss of electrons and these electrons are then consumed by water molecules to form hydrogen molecules. The interaction between the anodic and cathodic sites as described on the basis of mixed potential theory is represented by well-known relationships using current (reaction rate) and potential (driving force). For the above pair of electrochemical reactions (anodic Eq. 2 and cathodic Eq. 3), the relationship between the applied current $I_a$ and applied potential, $E_a$, follows the Butler-Volmer equation, $$I_a=I_{corr}(\exp[2.303(E_a-E_{corr})/\beta_a]-\exp[-2.303(E_a-E_{corr})/\beta_c]), \quad (4)$$

where $\beta_a$ and $\beta_c$ are the anodic and cathodic Tafel parameters given by the slopes of the polarization curves $\partial E_a/\partial \log_{10} I_a$ in the anodic and cathodic Tafel regimes, respectively and $E_{corr}$ is the corrosion, or open circuit potential.

The corrosion current, $I_{corr}$, cannot be measured directly. However, a-priori knowledge of $\beta_a$ and $\beta_c$ along with a small signal analysis technique, known as polarization resistance, can be used to indirectly compute $I_{corr}$. The polarization resistance technique, also referred to as linear polarization, is an experimental electrochemical technique that estimates the small signal changes in $I_a$ when $E_a$ is perturbed by $E_{corr}\pm 10$ mV. The slope of the resulting curve over this range is the polarization resistance, $$R_p \triangleq (\partial E_a/\partial I_a)|_{|E_a-E_{corr}|\leq 10 \, mV}. \quad (5)$$

ASTM standard G59 outlines procedures for measuring polarization resistance. Potentiodynamic, potential step, and current-step methods can be used to compute $R_p$. The potentiodynamic sweep method is the most common method for measuring $R_p$. A potentiodynamic sweep is conducted by applying $E_a$ between $E_{corr}\pm 10$ mV at a slow scan rate, typically 0.125 mV/s. A linear fit of the resulting $E_a$ vs. $I_a$ curve is used to compute $R_p$.

Note, the applied current, $I_a$, is the total applied current and is not multiplied by the electrode area, so $R_p$ as defined in (5) has units of $\Omega$. Provided that $|E_a-E_{corr}|/\beta_a\leq 0.1$ and $|E_a-E_{corr}|/\beta_c\leq 0.1$, the first order Taylor series expansion $\exp(x)\cong 1+x$ can be applied to Eq. 4 and Eq. 5 to arrive at, $$I_{corr}=B/R_p, \quad (6)$$

where $B=\beta_a\beta_c/(2.303(\beta_a+\beta_c))$ is a constant of proportionality. Therefore, knowledge of $R_p$, $\beta_a$ and $\beta_c$ enables direct determination of $I_{corr}$ at any instant in time. The mass loss due to corrosion, $M_{loss}$ as grams, is calculated from $I_{corr}$ with Faraday's constant, F, number of electrons lost per atom of the metal during an oxidation reaction, z, atomic weight, AW, and sample period, $T_s$:

$$M_{loss}=BT_s(AW/zF)\Sigma R_p^{-1}. \quad (7)$$

ASTM standard G59 outlines the procedure for measuring the Tafel slopes, $\beta_a$ and $\beta_c$. First, $E_{corr}$ is measured from the open circuit potential. Next, $E_a$ is initialized to $E_{corr}$–250 mV. Then, a potentiodynamic sweep is conducted by increasing $E_a$ from $E_{corr}$–250 mV to $E_{corr}$+250 mV at a slow scan rate, typically 0.125 mV/s. Next, a Tafel curve is plotted for $E_a$ vs. $\log_{10} I_a$. Values for $\beta_a$ and $\beta_c$ are estimated from the slopes of the linear extrapolated anodic and cathodic currents.

Some implementations discussed herein directly monitor the corrosion of the structure using a three electrode device without introducing galvanic corrosion to the electrode structures, rather than measuring corrosion indirectly between two electrodes by measuring the corrosion rate of the same material as the structure local to the sensor only and not the corrosion of the structure itself. One benefit is that the amount of corrosion or mass loss measured is not limited by the electrode thickness, therefore electrodes as described previously having thickness of, e.g., 1-20 mils may be capable of measuring corrosion mass losses in excess of several millimeters. An additional benefit is that since the sensor is fabricated from an inert metal, the time of wetness and salinity can be independently measured across the pair of interdigitated electrodes.

Electrode

FIG. 1 is a schematic diagram of a micro linear polarization resistance flex sensor consistent with one or more aspects of the innovations herein. FIG. 1 illustrates a microfabricated sensor device placed on a flex-cable circuit 10 useful for directly monitoring deterioration of a structure due to corrosion. The device includes three electrodes 16, 18, 20. Each electrode is fabricated on a flex circuit consisting of a noble metal, typically gold-plated copper. The working electrode 16 is placed 10 mm or less from the counter and reference electrodes. The reference electrode 18 and the counter electrode 20 are fabricated with a thickness of 1-10 mils and a length of 0.1-20 mm. The electrodes are configured in an interdigitated fashion with a separation distance of 10 mils or less. The reference, counter and working electrodes may be reconfigured through the use of jumpers 14.

Flex Cable Attachment

FIG. 2 is a schematic diagram of an illustrative micro linear polarization resistance flex sensor attached to the structure consistent with one or more aspects of the innovations herein. The μLPR flex sensor 10 in FIG. 2 may make electrical contact to the structure by placing a ~1 mil thick electrically conductive transfer tape 22 between the working electrode 16 and structure 26. Other methods that provide a conductive contact between the working electrode may utilize conductive epoxies or solders so long as acceptable ohmic contacts are obtained and the process does not impact the flex cable. The μLPR flex sensor 10 may contain an insulating/porous scrim material 24 between both the reference electrode 18 and counter electrode 20 and the structure 26. The μLPR flex sensor 10 may be attached to the structure 26 through the use of adhesives or in the case of placement in a butt joint or lap joint configuration, the holding force is provided by the joint itself.

Analog Instrumentation

FIG. 3 is a schematic diagram of illustrative instrumentation amplifier circuitry that may be used in the sensor device consistent with one or more aspects of the innovations herein. FIG. 3 is a schematic of the electronic instrumentation 28. The applied potential signal is generated by the microprocessor 30 and may be converted into an analog signal using a Digital-to-Analog Converter (DAC) 32. A voltage follower amplifier 34 may be used to set the applied potential across the counter electrode 20 with respect to virtual ground. A switch 40 may be used to disable the applied voltage. A single pull double throw switch 36 may be used to determine which electrodes the reference potential is measured between. When the switch 36 is normally closed, the reference potential is measured between the counter electrode 20 and the working electrode 16. When the switch 36 is in the alternate state, the reference potential is measured between the reference electrode 18 and the working electrode 16. In both cases, the reference potential may be measured using a differential amplifier 38. Further, the applied current may be measured using a trans-resistance amplifier 42 with selectable gains 44, which can be configured by the microprocessor 30. The resulting reference potential and applied current measurements may be digitized by the Analog-to-Digital Converter (ADC) 46 and read by the microcontroller 30. When the switch 36 is in the default positions (normally closed), the microcontroller 30 computes the linear polarization resistance with respect to the structure 26. Alternatively, when the switch 36 is in the alternate position, the microcontroller 30 computes the linear polarization resistance with respect to the counter electrode 20 and working electrode 16 of the sensor 10.

While a specific example of microcontroller 30 as specified in FIG. 3 is a TI MSP-430, a generalized microcontroller unit will serve the functions described.

Embedded Hardware

Figure 4A:
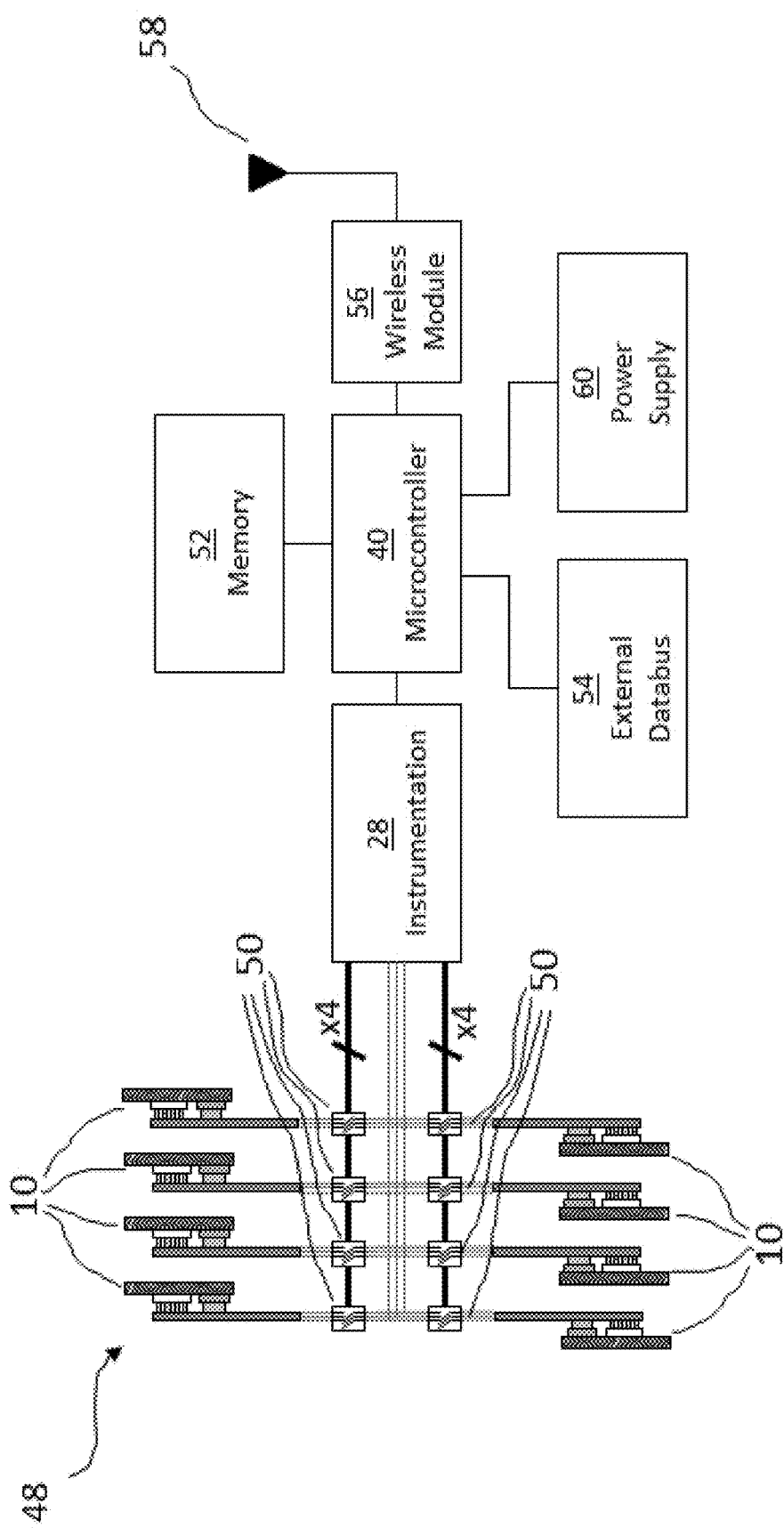
FIGS. 4A and 4B are block diagrams of an illustrative flex circuit device connected to embedded hardware consistent with one or more aspects of the innovations herein.
Figure 4B:
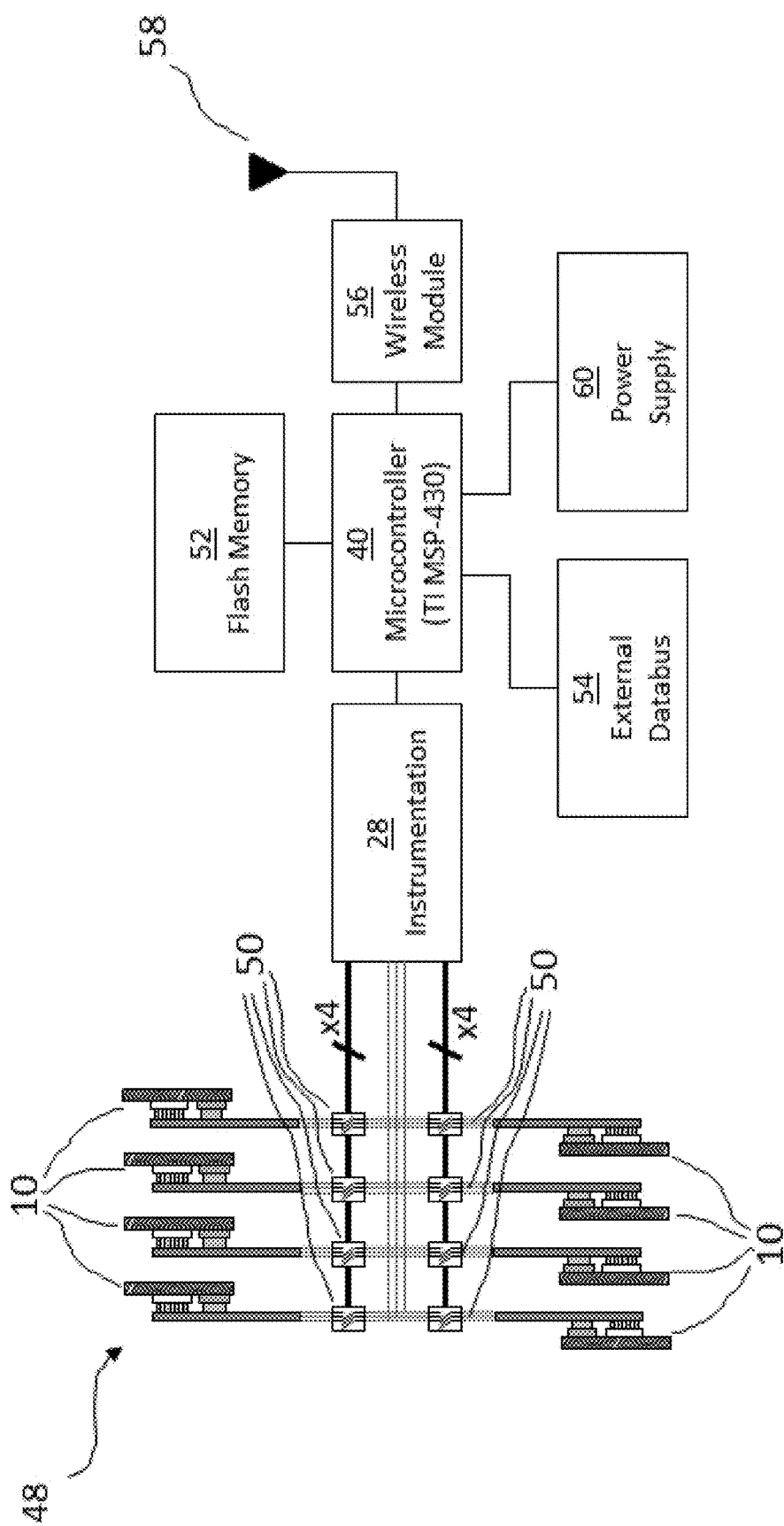

FIGS. 4A and 4B are block diagrams of illustrative flex circuit devices connected to embedded hardware consistent with one or more aspects of the innovations herein. FIG. 4A is a diagram of the embedded hardware system 48. The microcontroller 40 may coordinate data collection and data processing as described above, data transmission, and data storage. For example, the microcontroller (e.g., TI MSP-430 or the like) may interrogate the array of µLPR flex sensors 10 and collects readings through the instrumentation circuitry 28. In some implementations, the microcontroller determines by channel selection which of the sensors is active through a set of multiplexed switches 50. The microcontroller 40 computes resistances from the applied current and reference potentials and stores the resulting values to memory 52. In a more specific embodiment as illustrated in FIG. 4B, the microcontroller 40 may compute resistances from the applied current and reference potentials and stores the resulting values in internal flash memory 52. Referring to both FIG. 4A and FIG. 4B, sensor data can be downloaded or acquired through an external data bus 54 or using a wireless module 56 to transmit the data via an antenna 58. The power supply 60 can consist of an internal battery, rechargeable battery (such as lithium-ion) and/or power from an external source, including energy harvesting elements.

Signal Measurement

Figure 5A:
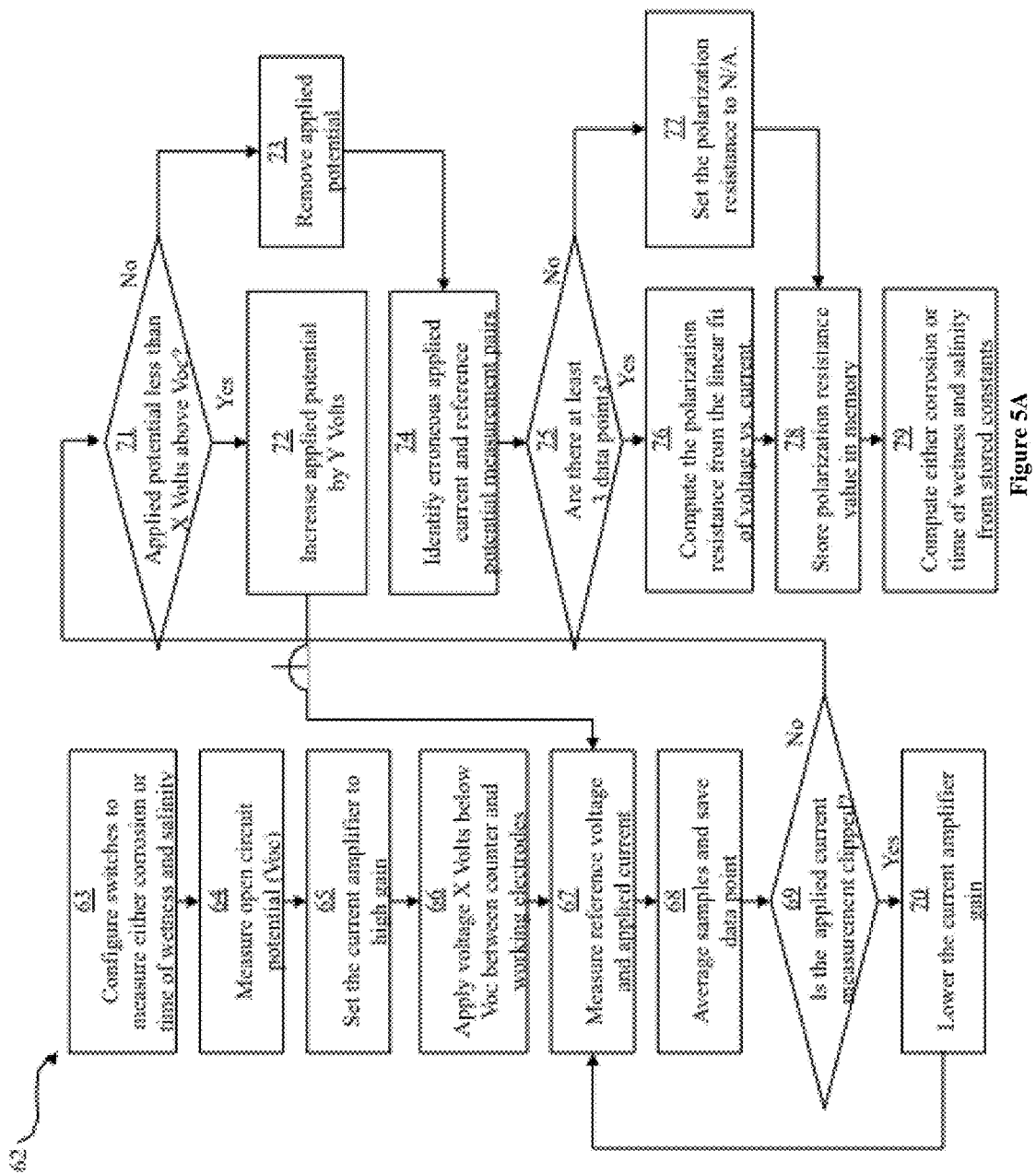
FIGS. 5A and 5B are flow diagrams showing illustrative processes for computing either the corrosion rate from linear polarization resistance or the time of wetness and salinity consistent with one or more aspects of the innovations herein.

FIG. 5A is an exemplary flow diagram for computing either the corrosion rate from linear polarization resistance or the time of wetness and salinity consistent with one or more aspects of the innovations herein. The process to measure the polarization resistance from the instrumentation amplifiers is illustrated in the illustrative flowchart of FIG. 5A. First, the single pull double throw switch 36 is configured to measure either the LPR with respect to the structure 26 or between the counter 20 and working 16 electrodes of the LPR sensor 10 (step 63). The open circuit potential is measured as the reference potential when the applied voltage is disabled (step 64). The gain for the current amplifier is initially set high (step 65). Then, the applied potential is enabled and set in fixed incremental steps of finite time duration starting X Volts below the open circuit potential (step 66). According to some implementations, the amount of time between each step may be in the 5 ms to 100 ms range, and not necessarily limited to this range depending on the amplifier circuitry and electrode configuration being utilized. Once the step is applied, the applied current is measured from the resulting signal along with the reference potential measured between the reference electrode and the working electrode (step 67). Multiple samples are acquired from both waveforms and averaged together to reduce noise (step 68). Next, the measured applied current is evaluated for clipping (step 69). According to this illustrative implementation, if the applied current is within 5% of the upper or lower ranges of the amplifier, the current gain is lowered and the measurement is repeated (step 70). Otherwise, the applied potential is evaluated to determine if it is below X volts above the open circuit potential (step 71). If so, then the applied potential is incremented by Y Volts, where for example, $X/10 < Y < X/5$, and another measurement of the applied current and reference potential is taken (step 72). Otherwise, the scan is complete and the applied potential is disabled (step 73). All of the recorded applied current and reference potential measurement/data point pairs points are verified. Any erroneous data points that demonstrate any irregularity (for example, clipped by the amplifier) are omitted (step 74). Then, the number of valid data points is checked to ensure there are at least three to perform a linear fit (step 75). If there is, then the polarization resistance is determined by performing a linear fit of the verified reference potential vs. applied current data points (step 76). Otherwise, the polarization resistance is reported as N/A (step 77). In both cases, the resulting polarization resistance value is stored in internal memory (step 78). Finally, depending on the electrode configuration using switch 40, either the corrosion rate and total corrosion or time of wetness and salinity is computed from stored constants (step 79).

Figure 5B:
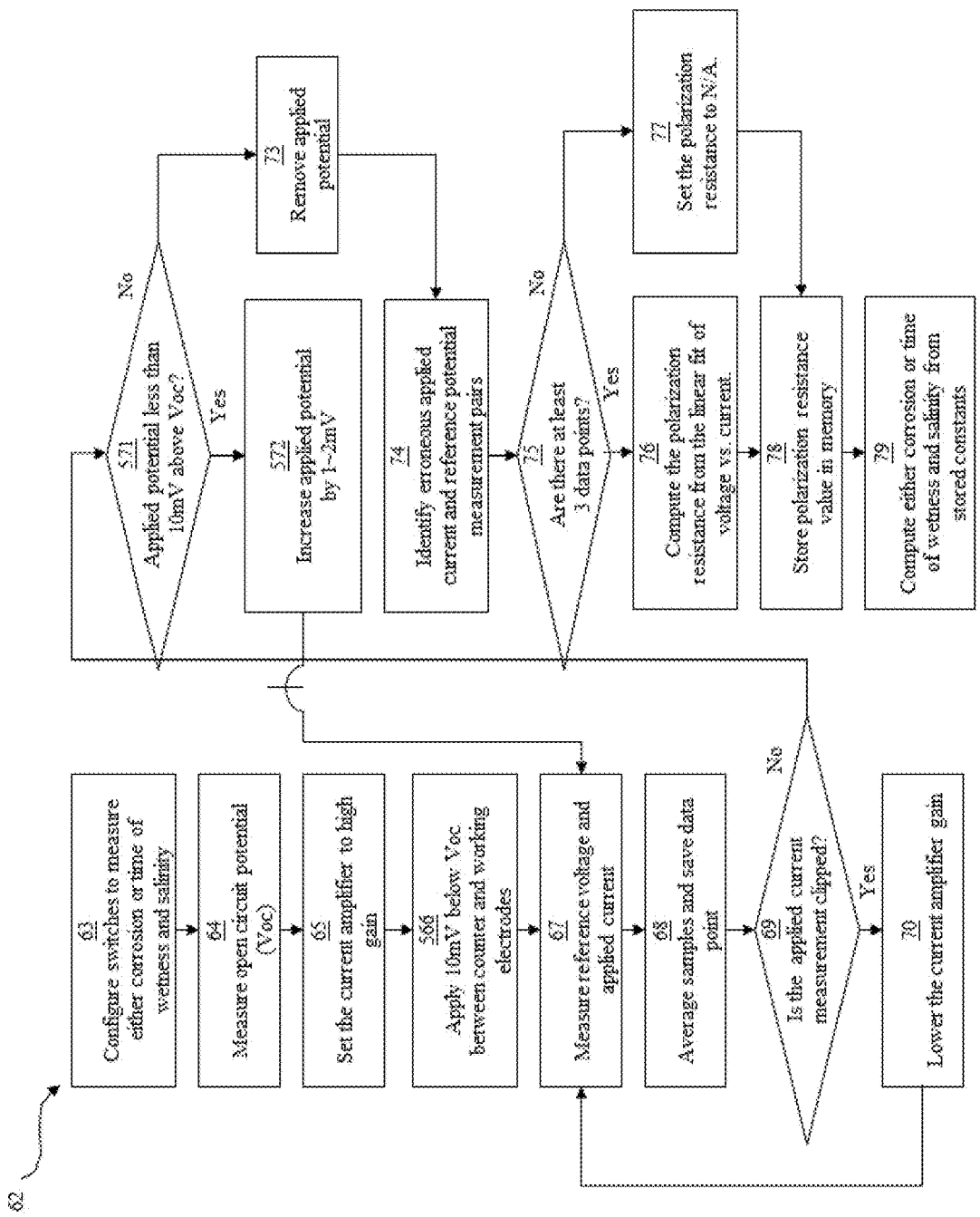

FIG. 5B is another exemplary flow diagram for computing either the corrosion rate from linear polarization resistance or the time of wetness and salinity consistent with one or more specific aspects of the innovations herein. The process to measure the polarization resistance from the instrumentation amplifiers is illustrated in the illustrative flowchart of FIG. 5B. First, the single pull double throw switch 36 is configured to measure either the LPR with respect to the structure 26 or between the counter 20 and working 16 electrodes of the LPR sensor 10 (step 63). The open circuit potential is measured as the reference potential when the applied voltage is disabled (step 64). The gain for the current amplifier is initially set high (step 65). Then, the applied potential is enabled and set in fixed incremental steps of finite time duration starting at 10 mV below the open circuit potential (step 566). The amount of time between each step can be set anywhere from 5 ms to 100 ms. Once the step is applied, the applied current is measured from the resulting signal along with the reference potential measured between the reference electrode and the working electrode (step 67). Multiple samples are acquired from both waveforms and averaged together to reduce noise (step 68). Next, the measured applied current is evaluated for clipping (step 69). According to this illustrative implementation, if the applied current is within 5% of the upper or lower ranges of the amplifier, the current gain is lowered and the measurement is repeated (step 70). Otherwise, the applied potential is evaluated to determine if is below 10 mV above the open circuit potential (step 571). If so, then the applied potential is incremented by 1-2 mV and another measurement of the applied current and reference potential is taken (step 572). Otherwise, the scan is complete and the applied potential is disabled (step 73). All of the recorded applied current and reference potential measurement/data point pairs points are verified. Any erroneous data points that demonstrate any irregularity (for example, clipped by the amplifier) are omitted (step 74). Then, the number of valid data points is checked to ensure there are at least three to perform a linear fit (step 75). If there is, then the polarization resistance is determined by performing a linear fit of the verified reference potential vs. applied current data points (step 76). Otherwise, the polarization resistance is reported as N/A (step 77). In both cases, the resulting polarization resistance value is stored in internal memory (step 78). Finally, depending on the electrode configuration using switch 40, either the corrosion rate and total corrosion or time of wetness and salinity is computed from stored constants (step 79).

Example 1: Verification of Corrosion Rate Using Lap Joints

Samples were cut to length and uniquely marked with stencil stamps close to the edge of both faces of the sample. The samples were then cleaned using an alkaline cleaner, TURCO 4215 NC-LT—50 g/L for 35 min at 65° C. Afterwards, the samples were rinsed with Type IV reagent grade deionized water and immersed in a solution of 20% (v/v) nitric acid for 15 min. The samples were then rinsed again in the deionized water and air dried. The weights were recorded to the nearest fifth significant figure and the samples were stored in a desiccator. After massing the samples were assembled in a lap-joint configuration and coated with 2 mils of epoxy-based primer and 2 mils of polyurethane.

Control samples, free of any corrosion, were weighed before and after being subjected to the same cleaning process as the corroded samples to determine the extent of metal loss resulting from the cleaning procedure. Corroded samples were lightly brushed with nylon bristles. The corroded samples were then placed in a solution of TURCO 4215 NC-LT—50 g/L for 1 hour at 65° C. Afterwards, in accordance with ASTM G1, the standard practice for preparing, cleaning and evaluating corrosion test specimens, the samples were placed in a solution of 50 mL of 85% (v/v) phosphoric acid, 20 g chromium trioxide and reagent water to make 1000 mL for 10 min at 90° C. Next, the samples were placed in 20% (v/v) nitric acid for 5 min at 20° C. The samples were rinsed first with the deionized water and then ethanol. Following the rinse, the samples were air dried and stored in a desiccator.

Figure 6:
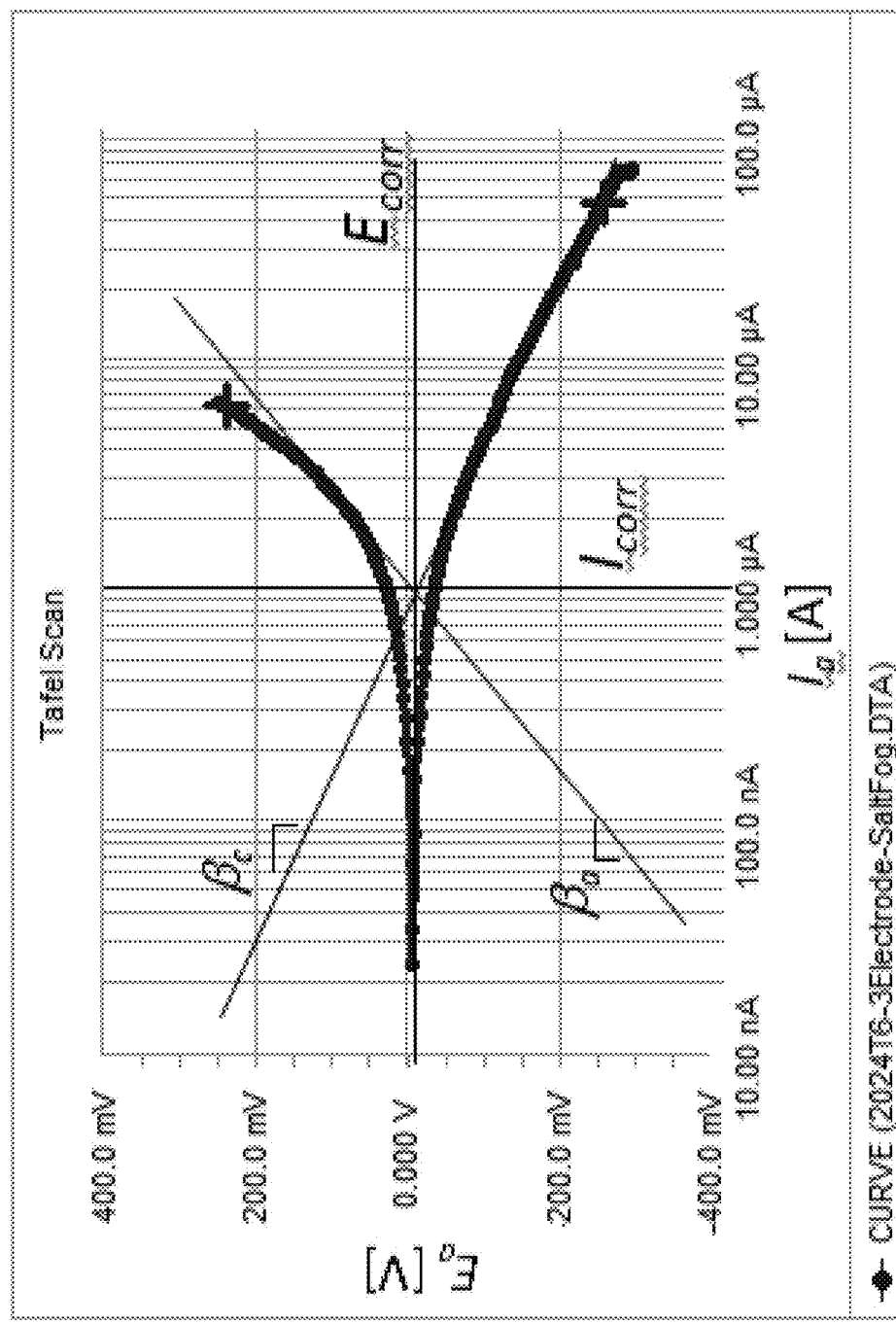
FIG. 6 is an example plot of a Tafel curve used to calibrate the Tafel constants for the lap-joint example consistent with one or more aspects of the innovations herein.

Corrosion tests were performed in a cyclic corrosion chamber running a modified B117 salt-fog test, specifically the ASTM G85-A5 test. This test consisted of two one hour steps. The first step involved exposing the samples to a salt fog for a period of one hour at 25° C. The electrolyte solution composing the fog was 0.05% sodium chloride and 0.35% ammonium sulfate in deionized water. This step was followed by a dry-off step, where the fog was purged from the chamber while the internal environment was heated to 35° C. Electrical connections for the flex sensors were made to an AN110 positioned outside the sealed chamber by passing extension cables through the bulkhead in the chamber. Temperature, relative humidity, and LPR data was acquired at 1 minute intervals. During the first cycle, the Tafel coefficients were acquired using a potentiostat (Gamry Reference 600) following the ASTM standard G59. FIG. 6 is an example plot of a Tafel curve used to calibrate the Tafel constants for the lap-joint example consistent with one or more aspects of the innovations herein. The coefficients were extrapolated from the $E_a$ vs. $\log_{10} I_a$ plots as shown in FIG. 6.

Figure 7A:
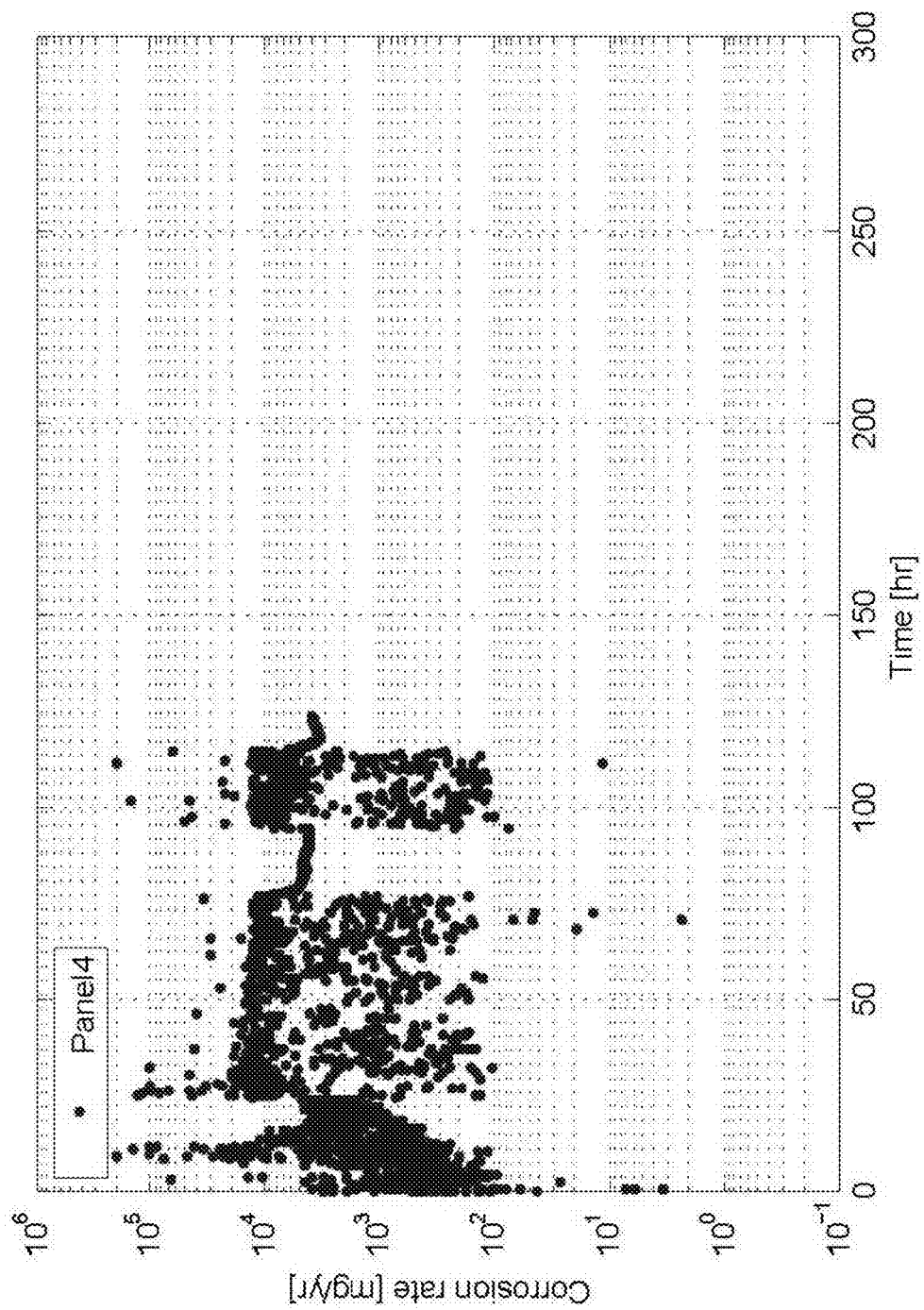
FIGS. 7A, 7B and 7C are example plots of corrosion rate vs. time converted from linear polarization resistance measurements consistent with one or more aspects of the innovations herein.
Figure 7B:
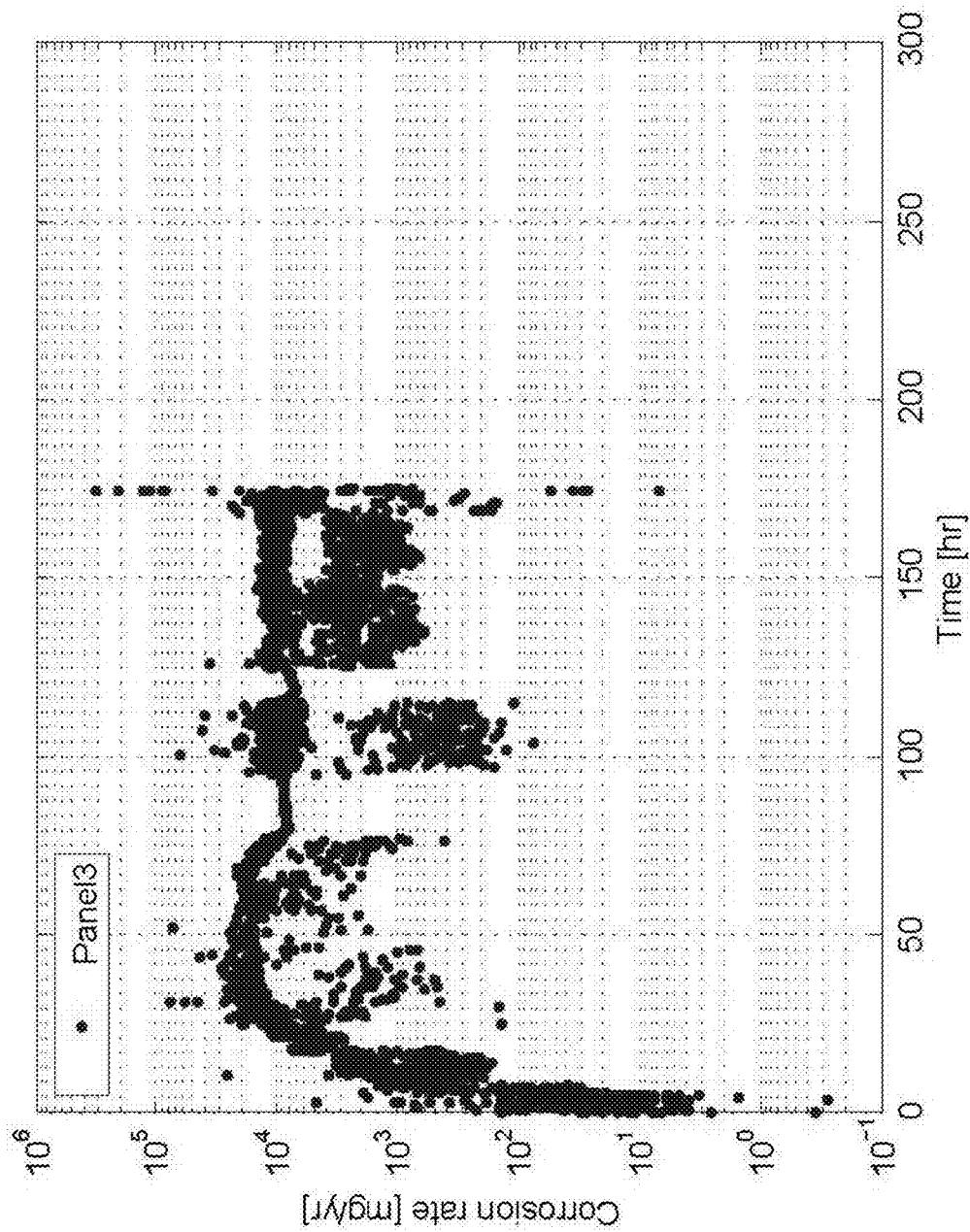
Figure 7C:
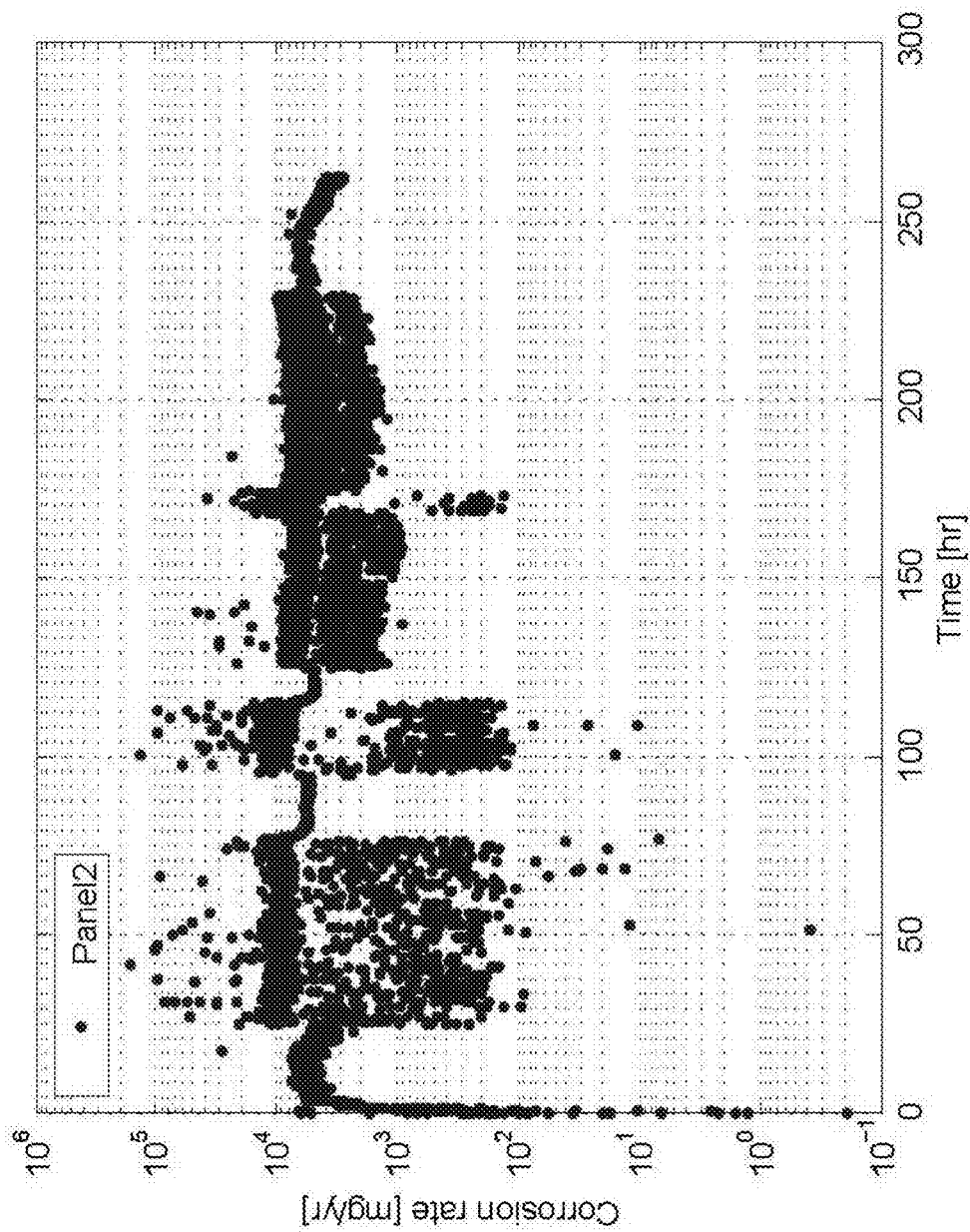

At the conclusion of this experiment lap joints were removed from the environmental chamber and disassembled. Following disassembly, the polyurethane and epoxy coatings on the aluminum panels were removed by placing them in a solution containing methyl ethyl ketone. After a 30 minute immersion the panels were removed and rinsed with deionized water. These panels were again alkaline cleaned with a 35 minute immersion into a constantly stirred solution of 50 g/l Turco 4215 NC-LT at 65° C. This was followed by a deionized water rinse and immersion into a 90° C. solution of 85% phosphoric acid containing 400 g/l chromium trioxide for 10 minutes. Following phosphoric acid treatment the panels were rinsed with deionized water and placed into a 20% nitric acid solution for 5 minutes at 25° C. Plates were then rinsed with deionized water, dipped in ethanol, and dried with a heat gun. This cleaning process was repeated until mass values for the panels stabilized. FIG. 7a, b, c are example plots of corrosion rate vs. time converted from linear polarization resistance measurements on 3 separate specimens subjected to different corrosion environments consistent with one or more aspects of the innovations herein. The corrosion rate was computed from the linear polarization resistance using the material properties and Tafel constants, shown in FIG. 6.

Figure 8:
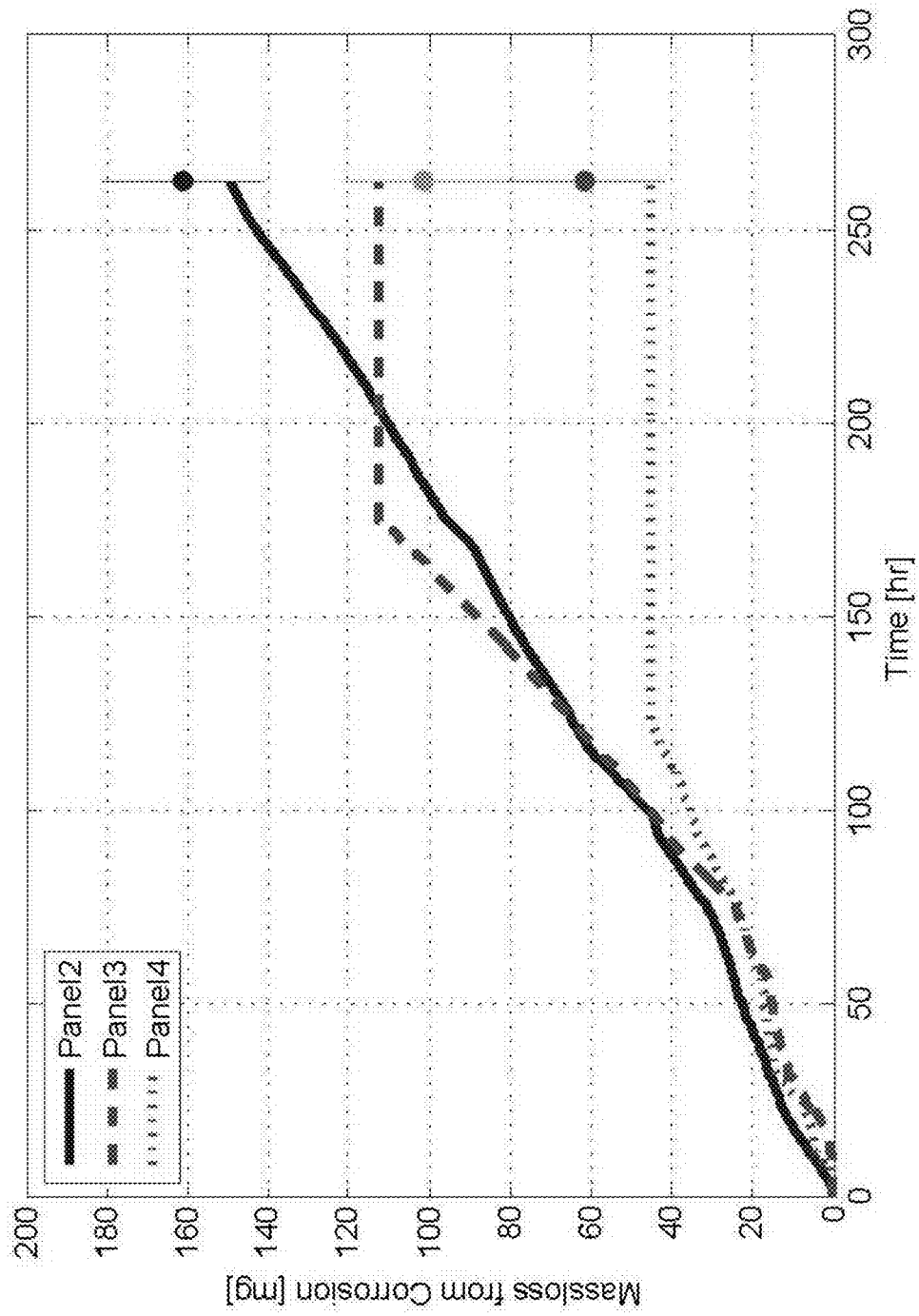
FIG. 8 is an example plot of corrosion as total mass loss computed from the linear polarization measurements vs. time and error bars of the measured mass loss after cleaning consistent with one or more aspects of the innovations herein.

FIG. 8 is an example plot of corrosion as total mass loss computed from the linear polarization measurements vs. time and error bars of the measured mass loss after cleaning consistent with one or more aspects of the innovations herein. The corrosion rate was converted to total corrosion as a measure of mass loss vs. time as shown in FIG. 8.

Figure 9:
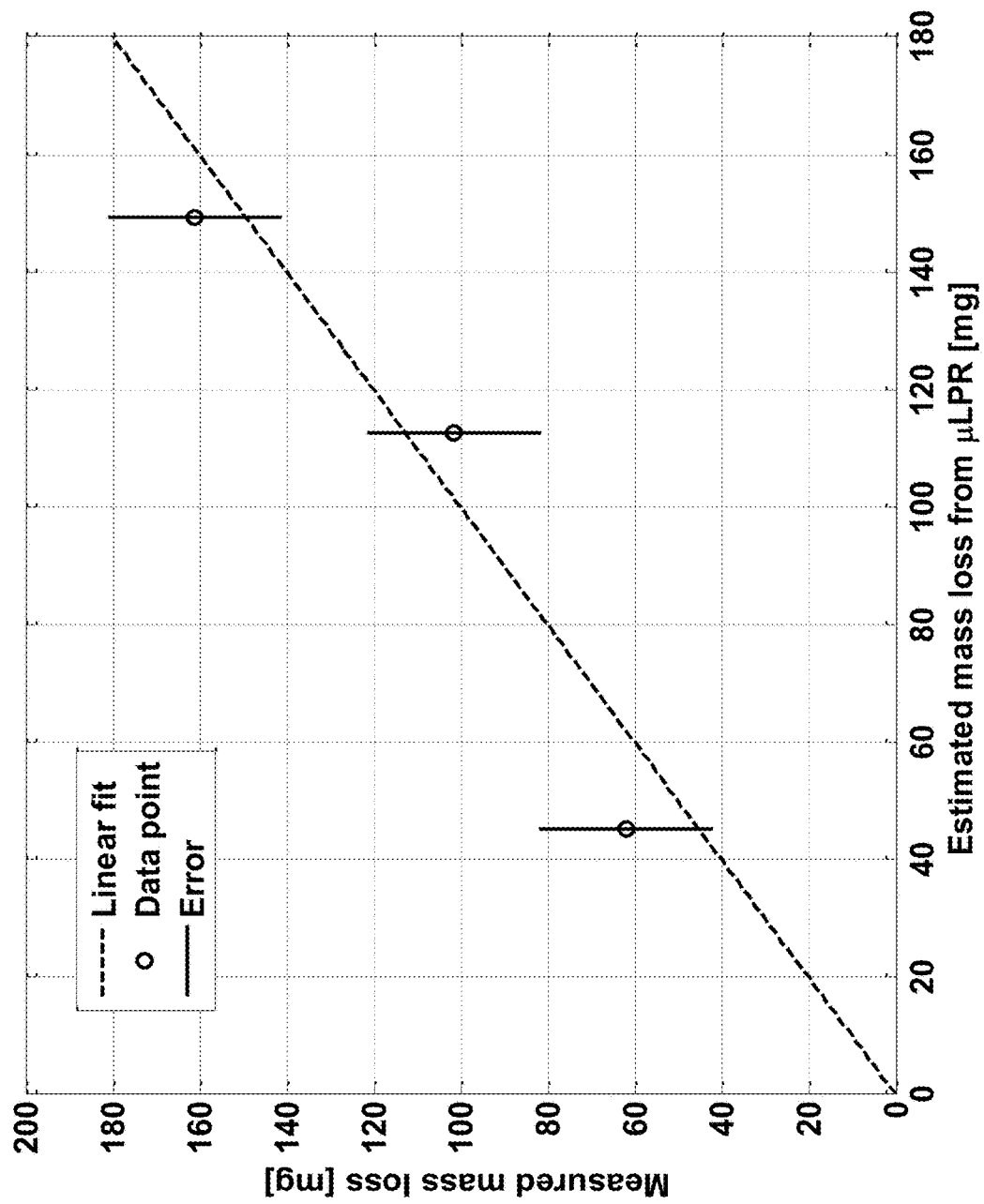
FIG. 9 is an example plot comparing measured vs. estimated mass loss using the sensor device consistent with one or more aspects of the innovations herein.

FIG. 9 is an example plot comparing measured vs. estimated mass loss using the sensor device consistent with one or more aspects of the innovations herein. The above values were then compared with values measured through traditional mass loss measurements by weighing the coupons before and after the corrosion process, shown in and FIG. 9. The results indicate the corrosion estimated from the sensors agreed to within the experimental error of the actual corrosion measured from the coupons.

Example 2: Verification of Time of Wetness Measurements

Figure 10:
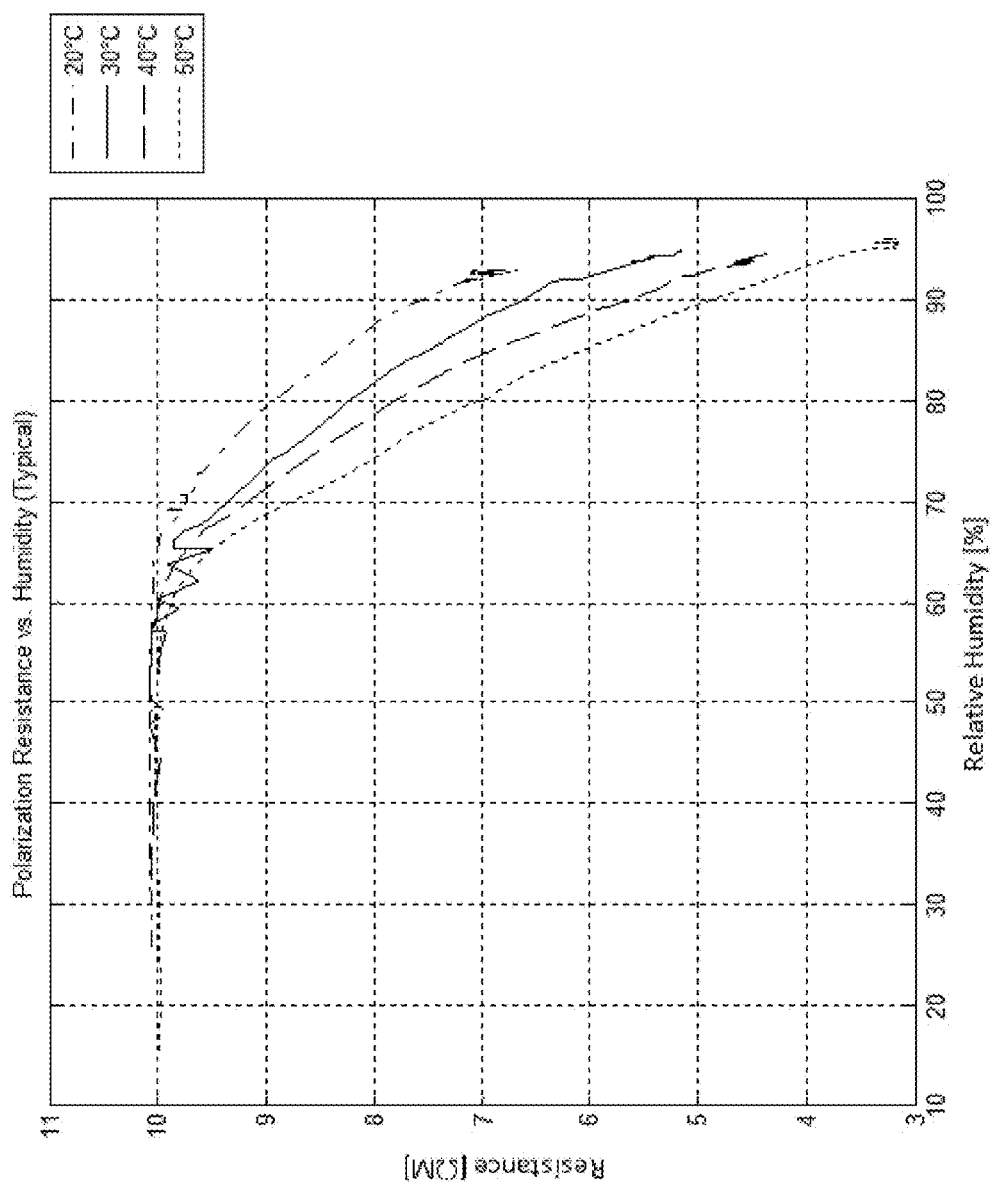
FIG. 10 illustrates calibration data of measured resistance vs. relative humidity measured between the two interdigitated electrodes for four different temperature conditions consistent with one or more aspects of the innovations herein.

FIG. 10 illustrates exemplary calibration data of measured resistance vs. relative humidity measured between the two interdigitated electrodes for four different temperature conditions consistent with one or more aspects of the innovations herein. By definition, the time of wetness is the amount of time elapsed when the relative humidity is at least 80%. FIG. 10 shows the relationship between the measured resistance between the counter and reference electrodes for different values of relative humidity for four different temperature conditions. The data was collected using a calibrated environmental temperature/humidity chamber (TestEquity 123H). The time of wetness is determined by setting a threshold value for the resistance corresponding to the point at which the relative humidity is at least 80%. Then, the time of wetness is computed as the amount of time the resistance was recorded below the threshold. According to the calibration data, the threshold can vary between 7MΩ to 9MΩ based on temperature. If the temperature variation is small, for example 20° C. to 30° C., the resistance threshold can be set at 8.5MΩ (±4%) which corresponds to 80% humidity (±4%). If the temperature variation is larger, for example 20° C. to 50° C., the resistance threshold can be set at 8MΩ (±15%) which corresponds to 80% humidity (±7%). For field applications this error is acceptable as in most cases the relative humidity will approach 100%, or saturation, when water is present between the electrodes of the device.

Example 3: Verification of Salinity Measurements

Figure 11:
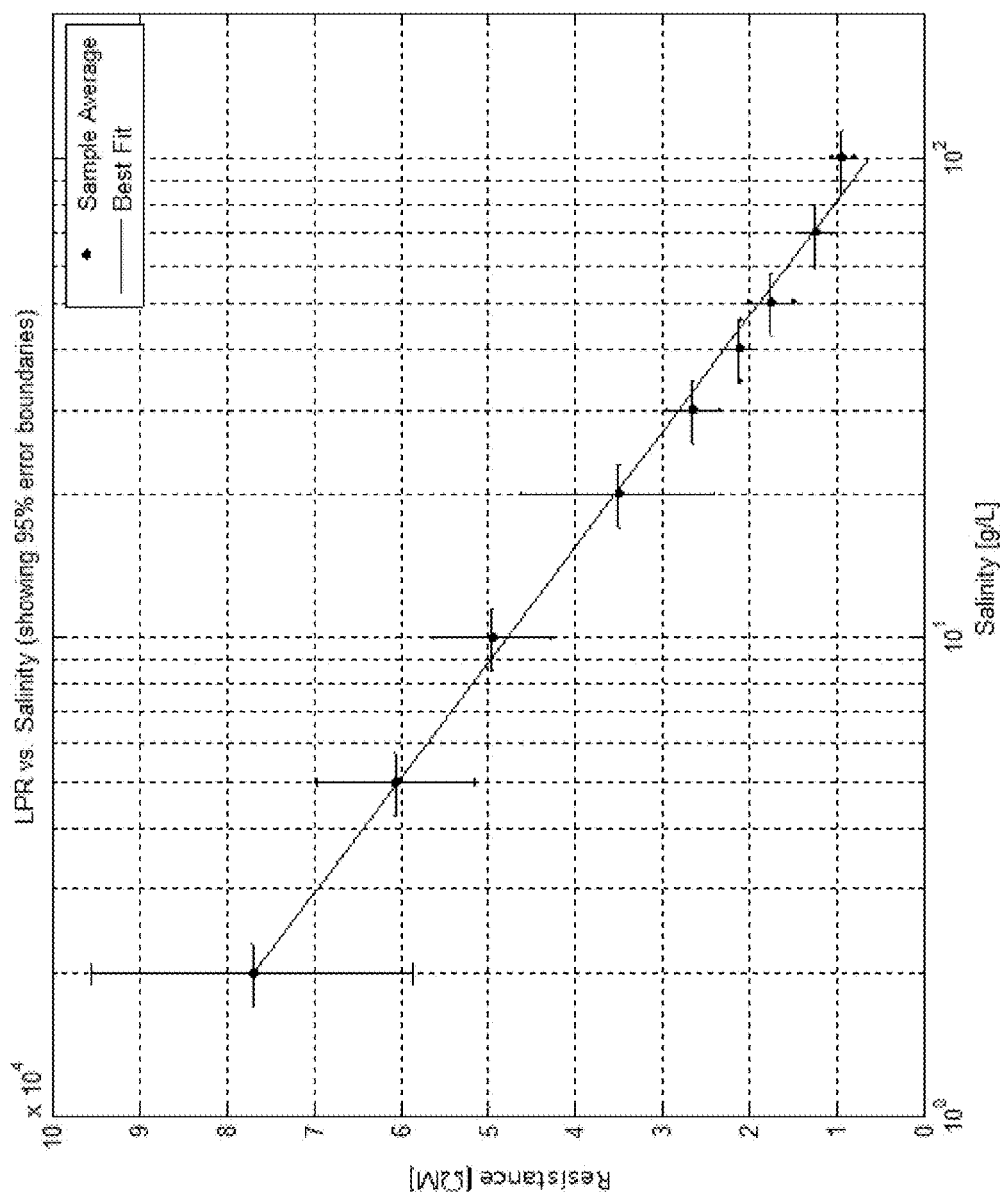
FIG. 11 illustrates calibration data of measured resistance vs. salinity measured between the two interdigitated electrodes consistent with one or more aspects of the innovations herein.

FIG. 11 illustrates calibration data of measured resistance vs. salinity measured between the two interdigitated electrodes consistent with one or more aspects of the innovations herein. By definition, salinity is measured as the ratio of the amount of salt (in grams) dissolved in a liter (or kilogram) of water. Units can also be expressed in parts per thousand. FIG. 11 shows calibration data from an experiment which eight separate sensors were placed in a beaker with a stir bar with 500 mL of distilled water. Sodium chloride Fcc/usp grade 99.8% was weighed using an analytical balance and added to the beaker in incremental amounts. The average resistance measured between the interdigitated electrodes was computed along with the standard deviation and plotted in a log plot in FIG. 11 as resistance vs. salinity. An empirical relationship was derived from a linear fit of resistance vs. the log of salinity. Using this relationship, the salinity can be inferred from a measure of resistance.

Other Aspects

Unless the context clearly requires otherwise, throughout the description and elsewhere herein, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

Although certain presently preferred implementations of the invention have been specifically described herein, it will be apparent to those skilled in the art to which the inventions pertain that variations and modifications of the various implementations shown and described herein may be made without departing from the spirit and scope of the innovations herein. Accordingly, it is intended that the inventions be limited only to the extent required by the applicable rules of law.

The invention claimed is:

1. A system for monitoring corrosion in a structure, the system comprising:
    a linear polarization resistance (LPR) sensor comprising a plurality of electrodes;
    instrumentation circuitry coupled to the LPR sensor, the instrumentation circuitry configured to set an applied potential across a first electrode and ground, selectively enable and disable the set potential, and select two of the electrodes across which potential is to be measured; and
    microcontroller circuitry coupled to the instrumentation circuitry, the microcontroller circuitry configured to generate the applied potential, measure an open circuit reference potential, measure the potential across the selected electrodes, adjust the applied potential, and determine a polarization resistance based on the measured potentials,
    wherein the plurality of electrodes comprises a working electrode, a reference electrode, and a counter electrode; and
    wherein the reference potential is measured between the counter electrode and the working electrode.

2. The system of claim 1, further comprising a plurality of LPR sensors coupled to the instrumentation circuitry.

3. The system of claim 1, wherein the first electrode is the counter electrode.

4. The system of claim 1, wherein the instrumentation circuitry further comprises a switch configured to select the two electrodes across which the potential is to be measured.

5. The system of claim 4, wherein the switch is a single pull double throw switch.

6. The system of claim 4, wherein the microcontroller circuitry is further configured to operate the switch.

7. The system of claim 1 wherein the instrumentation circuitry further comprises a switch configured to selectively enable and disable the set potential.

8. The system of claim 1 wherein the instrumentation circuitry further comprises an amplifier configured to set the applied potential.

9. The system of claim 8, wherein the microcontroller circuitry is further configured to supply a signal to the amplifier to generate the applied potential.

10. The system of claim 9, wherein the instrumentation circuitry further comprises a digital to analog converter (DAC) configured to receive the signal from the microcontroller circuitry, convert the received signal to an analog signal, and supply the analog signal to the amplifier.

11. The system of claim 8, wherein the microcontroller circuitry is further configured to control a gain of the amplifier to generate the applied potential.

12. The system of claim 1 wherein the instrumentation circuitry further comprises an analog to digital converter (ADC) configured to convert reference potential and measured potential signals from the LPR sensor to digital signals and supply the digital signals to the microcontroller circuitry.

13. The system of claim 1 wherein the microcontroller circuitry is configured to determine corrosion by:
    selecting the two electrodes a cross across which potential is to be measured via the instrumentation circuitry;
    disabling the set potential via the instrumentation circuitry;
    measuring the open circuit potential via the instrumentation circuitry;
    enabling the set potential via the instrumentation circuitry;
    setting the set potential in fixed incremental steps;
    for each set potential, measuring the applied potential;
    for each measured applied potential, evaluating the measured potential to determine its value relative to the open circuit potential;
    determining polarization resistance based on a linear fit of the open circuit potential vs. each evaluated measured potential; and
    computing at least one of a corrosion rate, total corrosion, time of wetness, and time of salinity based on the polarization resistance.

14. The system of claim 1 further comprising a memory coupled to the microcontroller circuitry.

15. The system of claim 14, wherein the memory is a flash memory.

16. The system of claim 14, wherein the memory stores constants used in the determining of the corrosion.

* * * * *